United States Patent
Beckers et al.

(10) Patent No.: US 11,627,938 B2
(45) Date of Patent: Apr. 18, 2023

(54) IMAGING DEVICE WITH ULTRASOUND TRANSDUCER ARRAY

(71) Applicant: KONINKLIJKE PHILIPS N.V., Eindhoven (NL)

(72) Inventors: Lucas Johannes Anna Maria Beckers, Veldhoven (NL); Vincent Adrianus Henneken, Utrecht (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1055 days.

(21) Appl. No.: 16/329,048

(22) PCT Filed: Aug. 22, 2017

(86) PCT No.: PCT/EP2017/071067
§ 371 (c)(1),
(2) Date: Feb. 27, 2019

(87) PCT Pub. No.: WO2018/041658
PCT Pub. Date: Mar. 8, 2018

(65) Prior Publication Data
US 2019/0192116 A1 Jun. 27, 2019

(30) Foreign Application Priority Data
Aug. 30, 2016 (EP) .................. 16186332

(51) Int. Cl.
*A61B 8/00* (2006.01)
*B06B 1/02* (2006.01)
*A61B 8/08* (2006.01)
*G10K 11/02* (2006.01)
(Continued)

(52) U.S. Cl.
CPC .......... *A61B 8/4281* (2013.01); *B06B 1/0292* (2013.01); *C09D 7/48* (2018.01);
(Continued)

(58) Field of Classification Search
CPC ....... A61B 8/4281; A61B 8/12; A61B 8/4494; A61B 8/445; A61B 8/488; B06B 1/0292;
(Continued)

(56) References Cited

U.S. PATENT DOCUMENTS 4,756,313 A 7/1988 Terwilliger
5,817,015 A 10/1998 Adair
(Continued)

FOREIGN PATENT DOCUMENTS

CN 104367345 A 2/2015
JP 2005013453 A 1/2005
(Continued)

OTHER PUBLICATIONS

Chang, et al., "Acoustic lens for capacitive micromachined ultrasonic transducers", Journal of Micromechanics & Microengineering, Institute of Physics Publishing, Bristol, GB, vol. 24, No. 8, Jul. 15, 2014, pp. 1-13.

*Primary Examiner* — Joseph M Santos Rodriguez
*Assistant Examiner* — Kaitlyn E Sebastian (57) ABSTRACT

An imaging device (100) is disclosed comprising an ultrasound transducer array (101, 120, 130) having a plurality of ultrasound transducer elements defining an ultrasound emitting surface of the ultrasound transducer array; and an acoustic window (220) on the ultrasound emitting surface, said acoustic window comprising: a first layer (221) of a hydrocarbon elastomer contacting the ultrasound emitting surface, said first layer further containing an antioxidant; and a second layer (223) of a further hydrocarbon elastomer on the first layer, said second layer having a greater Shore A hardness than the first layer. Also disclosed are an ultrasound imaging system (10) comprising such an imaging device, such as catheter (100), and a method (300) of forming an
(Continued)

acoustic window (220) on an ultrasound transducer array (101, 120, 130) for such a device (100).

11 Claims, 5 Drawing Sheets (51) Int. Cl.
*C09D 109/00* (2006.01)
*C09D 7/48* (2018.01)
*A61B 8/12* (2006.01)

(52) U.S. Cl.
CPC ............ *C09D 109/00* (2013.01); *G10K 11/02* (2013.01); *A61B 8/12* (2013.01); *A61B 8/4494* (2013.01); *Y10T 29/49005* (2015.01)

(58) Field of Classification Search
CPC ........ C09D 7/48; C09D 109/00; G10K 11/02; Y10T 29/49005
See application file for complete search history.

(56) References Cited

U.S. PATENT DOCUMENTS

| | | |
|---|---|---|
| 7,303,374 B2 | 12/2007 | Ossmann |
| 8,997,590 B2 | 4/2015 | Oberdoerfer |
| 9,867,592 B2 | 1/2018 | Davidson |
| 2007/0161903 A1 | 7/2007 | Yamashita et al. |
| 2014/0265728 A1 | 9/2014 | Li et al. |

FOREIGN PATENT DOCUMENTS

| | | | |
|---|---|---|---|
| JP | 2007189342 A | 7/2007 | |
| JP | 2009066302 A | 4/2009 | |
| WO | 2016139087 A1 | 9/2016 | |
| WO | 2016139103 A1 | 9/2016 | |
| WO | WO-2016139087 A1 * | 9/2016 | ........... B06B 1/0292 |
| WO | WO-2016139103 A1 * | 9/2016 | ............... B06B 1/02 |

* cited by examiner

IMAGING DEVICE WITH ULTRASOUND TRANSDUCER ARRAY

This application is the U.S. National Phase application under 35 U.S.C. § 371 of International Application No. PCT/EP2017/071067 filed on Aug. 22, 2017, which claims the benefit of European Application Serial No. 16186332.9, filed Aug. 30, 2016. These applications are hereby incorporated by reference herein.

FIELD OF THE INVENTION

The present invention relates to an imaging device comprising an ultrasound transducer array having a plurality of ultrasound transducer elements defining an ultrasound emitting surface of the ultrasound transducer array; and an acoustic window on the ultrasound emitting surface.

The present invention further relates to an ultrasound imaging system comprising such an imaging device.

The present invention further relates to a method of forming such an acoustic window on the ultrasound emitting surface of an ultrasound transducer array for such an imaging device.

BACKGROUND OF THE INVENTION

Ultrasound imaging is an important diagnostic tool for imaging internals of the patient's body. This is typically achieved using one or more ultrasound transducer elements, typically organised in an ultrasound transducer array, which convert electrical energy into acoustic energy (ultrasound pulses) and convert the received pulse echoes back into electrical energy, which may be processed by a dedicated processing arrangement to convert the received electrical energy into ultrasound images.

Commonly used ultrasound transducer elements include piezoelectric-based ultrasound transducers (PZT) and capacitive micro-machined ultrasound transducers (CMUTs). These different types of transducers have in common that they require an acoustic matching material, commonly referred to as an acoustic window, between the ultrasound transducer elements and the patient's body in order to improve the acoustic performance of the ultrasound transducer elements by acoustic impedance matching of the emitting surfaces of the ultrasound transducer elements to the patient's body. An example of a CMUT assembly comprising such an acoustic window is disclosed in US 2016/0101437 A1.

The composition of such an acoustic window for ultrasound transducer arrays, e.g. ultrasound probes, to be applied to the skin of the patient is relatively straightforward, as the acoustic window does not have to meet stringent water barrier and thickness requirements that for instance are required when the ultrasound transducer array has to be operated for a longer period of time (such as monitoring) or within the body of the patient. One such application domain is catheters equipped with ultrasound imaging functionality, e.g. comprising a forward facing and/or side facing ultrasound transducer array. Such catheters must have a small form factor to facilitate penetration of small cavities, e.g. arteries or veins, within the body of the patient. At the same time, the ultrasound transducer arrays deployed with such catheters must be able to withstand the harsh environments, e.g. bodily fluids such as blood, stomach acid, and the like, in which case the acoustic window typically needs to provide additional protection to the ultrasound transducer elements of such an array. Another example the favorable application is ultrasound based patches, which configured for external use via a surface of a subject. These patches (low profile ultrasound probes) are configured to be used for a longer period of time (from hours to several days) and are desirable to withstand external body fluids such as sweat as well as a longer exposure to an acoustically coupling gel.

Materials that are commonly used for such imaging devices comprising ultrasound transducer arrays include silicone layers and soft polyurethane layers, as these materials have favourable acoustic properties bought have the disadvantage that they are not watertight. To this end, a covering layer of parylene is often added over the silicone or polyurethane layer to make the acoustic window watertight. However, this compromises the acoustic performance of the ultrasound transducer array due to the introduction of reflections and acoustic ringing problems associated with the interface between these two polymer layers.

SUMMARY OF THE INVENTION

The present invention seeks to provide a medical imaging device comprising an ultrasound transducer array having thereon a resilient thin acoustic window that is watertight and has improved acoustic characteristics.

The present invention further seeks to provide an ultrasound imaging system comprising such an imaging device.

The present invention yet further seeks to provide a method of forming such an acoustic window and the ultrasound transducer array for an imaging device.

According to an aspect, there is provided an imaging device such as catheter, said device comprising an ultrasound transducer array having a plurality of ultrasound transducer elements defining an ultrasound emitting surface of the ultrasound transducer array; and an acoustic window on the ultrasound emitting surface, said acoustic window comprising a first layer of a hydrocarbon elastomer contacting the ultrasound emitting surface, said first layer further containing an antioxidant; and a second layer of a further hydrocarbon elastomer on the first layer, said second layer having a greater Shore A hardness than the first layer.

The present invention is based on the insight that hydrocarbon elastomers, e.g. hydrocarbon thermosetting elastomers, are prone to gradual vulcanisation (oxidative cross-linking) through prolonged exposure to UV light or ambient environments containing oxidants, e.g. oxygen or water. Consequently, the inclusion of an antioxidant in a first layer of such an hydrocarbon elastomer of the acoustic window ensures that this first layer maintains its desired softness, which is desired to maximize the acoustic performance of the hydrocarbon elastomer, whilst the vulcanisation of the second layer, i.e. outer layer, of a further hydrocarbon elastomer of the acoustic window provides the desired watertight characteristic of the acoustic window and the consequential hardening of this second layer further provides improved protection of the ultrasound transducer array against accidental damage, e.g. scratching or the like.

In order to facilitate the selective hardening of the second layer, the second layer may not contain the (i.e. any) antioxidant, such that oxidation (weathering) of the second layer is not suppressed. The further hydrocarbon elastomer in the second layer may be actively cross-linked to accelerate the hardening of the second layer.

In further embodiments the imaging device is configured for external use via a surface of a subject or internal use within a subject. For external use configuration the imaging device preferably comprises an ultrasound probe or a patch enclosing the ultrasound transducer array. For internal use configuration the imaging device may comprise a catheter.

In an embodiment, the first layer has a thickness in a range of 5-10 micron as this is the minimum thickness at which the acoustic window achieves the desired acoustic impedance matching properties. The acoustic window may have a thickness of less than 100 micron and preferably less than 30 micron to make the acoustic window particularly suitable for catheter applications, i.e. to limit the dimensions of the catheter whilst achieving the desired acoustic properties of the acoustic window.

The hydrocarbon elastomer preferably is the same as the further hydrocarbon elastomer such that the acoustic properties of the first and second layers are closely matched. Polybutadiene is particularly suitable although other hydrocarbon elastomers, e.g. hydrocarbon copolymers, may be contemplated as alternatives to polybutadiene.

The first layer preferably has a Shore A hardness of less than 50 Shore, preferably less than 10 Shore, when measured with a durometer in accordance with the ASTM D2240 standard. This ensures good compliance with a moving ultrasound emitting surface, e.g. a membrane of a CMUT cell, whilst at the same time providing the first layer with a desirable acoustic impedance.

The antioxidant may be a phenolic stabilizer such as a stabilizer comprising a sterically hindered phenol head group and an aliphatic, e.g. hydrocarbon, tail, to facilitate blending of the antioxidant in the hydrocarbon elastomer.

The first layer may contain the antioxidant in an amount of 0.05%-0.5% by weight based on the total weight of the first layer. This amount of the antioxidant is sufficient to effectively suppress oxidation of the hydrocarbon elastomer in the first layer without significantly affecting the desired properties, e.g. acoustic impedance, of the first layer.

At least the first layer of the acoustic window may further comprise particles embedded in the hydrocarbon elastomer in order to tune the density and the acoustic impedance of the first layer, e.g. to minimize an acoustic impedance mismatch between the first layer and the body tissue to be exposed to ultrasound waves generated with the ultrasound transducer array. Such particles for example may be electrically insulating particles such as ceramic particles. The first layer may comprise the particles in an amount of 4-24% by weight based on the total weight of the first layer in order to tune the acoustic impedance of the first layer to a desired value.

In accordance with another aspect, there is provided an ultrasound imaging system comprising the imaging device of any of the herein described embodiments such an ultrasound imaging and control circuitry for controlling the ultrasound transducer array. Such an ultrasound imaging system, e.g. an ultrasound diagnostic imaging system, benefits from the inclusion of an imaging device according to an embodiment of the present invention by being able to generate high-resolution ultrasound images owing to the acoustic window on the ultrasound transducer array of the imaging device having favourable acoustic impedance properties as well as excellent mechanical properties.

According to yet another aspect, there is provided a method of forming an acoustic window on an ultrasound transducer array for an imaging device, the ultrasound transducer array having a plurality of ultrasound transducer elements defining an ultrasound emitting surface of the ultrasound transducer array, the method comprising depositing a first solution of a hydrocarbon elastomer and an antioxidant in an organic solvent on the ultrasound emitting surface; removing the organic solvent to form a first layer of the acoustic window contacting the ultrasound emitting surface, said first layer comprising the hydrocarbon elastomer and the antioxidant; depositing a second solution of a further hydrocarbon elastomer in a further organic solvent on the first layer and removing the further organic solvent to form a second layer of the acoustic window contacting the first layer, wherein the second layer has a greater Shore A hardness than the first layer.

This method facilitates the provision of ultrasound transducer array of an imaging device having an acoustic window that combines favourable acoustic impedance properties with excellent mechanical properties.

The method preferably further comprises cross-linking the further hydrocarbon elastomer in the second layer to increase the Shore A hardness of the second layer, such that the increased hardness of the second layer does not have to be the result of weathering of the second layer.

The solvent and the further organic solvent may be an alkane solvent such as heptane. Such solvents are particularly suitable for dissolving hydrocarbon elastomers and have the further benefit that they can be evaporated at relatively low temperatures due to the low vapour pressures of such solvents, such that the acoustic window may be formed without having to expose the ultrasound transducer array and the acoustic window layers to overly elevated temperatures, which may damage the ultrasound transducer array and/or the acoustic window layers.

The hydrocarbon elastomer preferably is the same as the further hydrocarbon elastomer. Polybutadiene is particularly suitable as polybutadiene has particularly favourable acoustic properties and may be readily oxidized (vulcanized) to form a second layer of the acoustic window having the desired mechanical and moisture barrier properties.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

It should be understood that the Figures are merely schematic and are not drawn to scale. It should also be understood that the same reference numerals are used throughout the Figures to indicate the same or similar parts.

Figure 1:
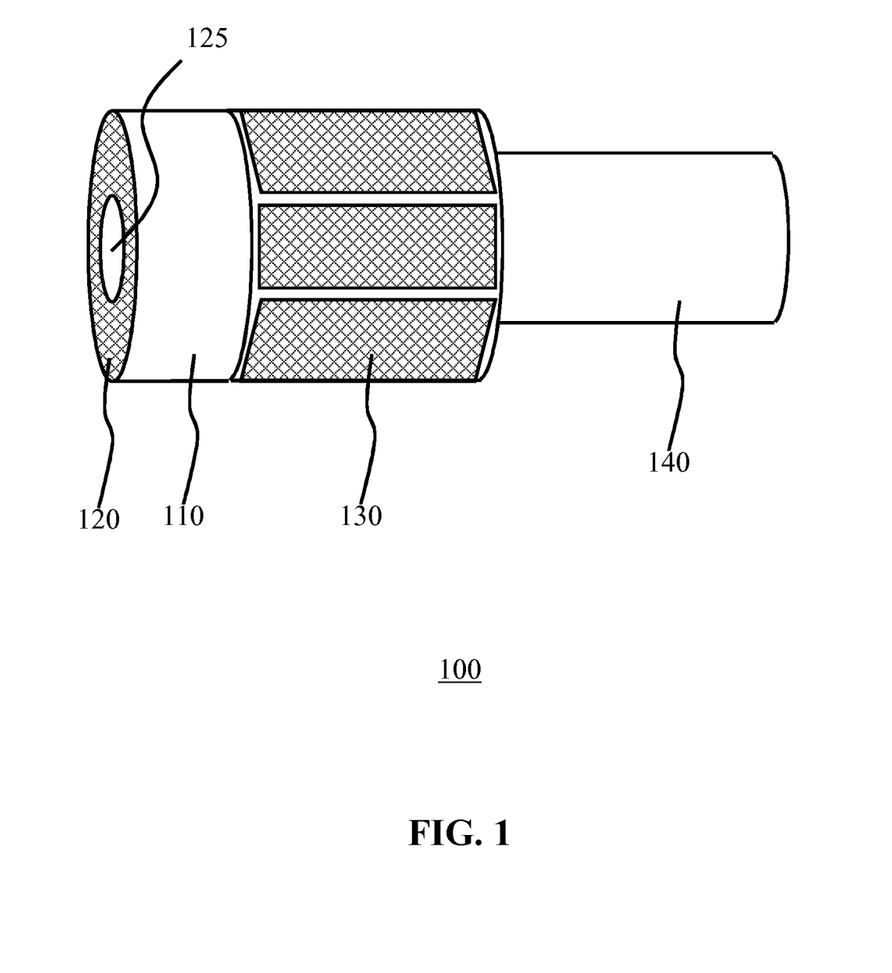
FIG. 1 schematically depicts a catheter as an example of an imaging device.

FIG. 1 schematically depicts an example embodiment of an imaging device: a catheter 100. The catheter 100 has a forward facing array 120 of ultrasound transducer elements mounted on the tip 110 of the catheter 100. The forward facing array 120 for example may be an IC chip carrying the ultrasound transducer elements, which may be mounted on the tip 110 in any suitable manner, e.g. gluing. The forward facing array 120 may include an aperture or channel 125 to facilitate an instrument (not shown) to extend through the tip of the catheter, e.g. for extracting a tissue sample from the patient for biopsy purposes. The catheter 100 may further comprise an arrangement of ultrasound transducer elements 130 wrapped around a side wall of the catheter 100, thereby facilitating a close to 360° field of ultra-sound vision of the catheter 100. In some embodiments the catheter can include only the side looking arrangement of the elements 130. This for instance may be achieved by providing islands or chips 130 carrying one or more ultrasound transducer elements interconnected by a flexible strip or the like that facilitates the wrapping of the respective islands or chips 130 around the catheter side wall. As such flexible arrangements are well-known per se, this will not be explained in further detail for the sake of brevity. The forward facing array 120 and the islands or chips 130 may contain any suitable number and type of ultrasound transducer elements benefiting from an acoustic window according to embodiments of the present invention as will be explained in further detail below. For example, the ultrasound transducer elements may be CMUT elements, PZT elements, and so on. The catheter tip 110 may be connected to a guide wire 140 or the like, to facilitate maneuvering the catheter tip 110 to the desired location within a patient's body.

It should be understood that embodiments of the present invention are not limited to the depicted example embodiment of the catheter 100. For example, it is equally feasible for the catheter 100 to only comprise one or more forward facing ultrasound transducer elements or to only comprise one or sideways facing ultrasound transducer elements. Similarly, the aperture or channel 125 may not be present, and so on. Embodiments of the present invention may be applied to any catheter design comprising any number of ultrasound transducer elements carrying an acoustic window according to an embodiment of the present invention.

Figure 2:
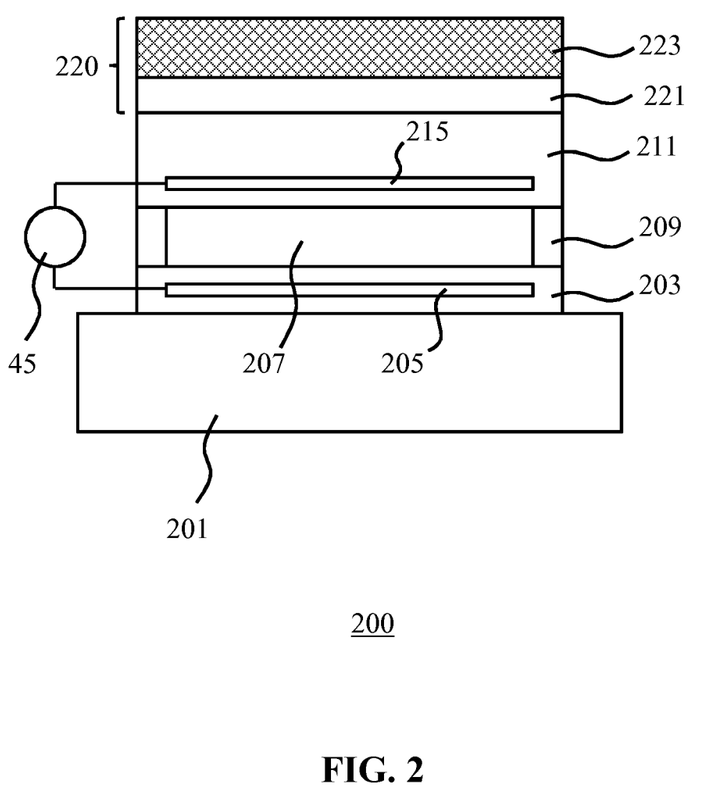
FIG. 2 schematically depicts an aspect of an imaging device according to an example embodiment.

In further embodiments the imaging device may be configured for external use via a surface of a subject or internal use within a subject (not shown). In this case the imaging device might include an ultrasound probe (preferably low profile ultrasound probe) comprising an acoustic window 220 coupled to an ultrasound emitting surface of said probe and described in more detail below. FIG. 2 schematically depicts an ultrasound transducer element 200 (here a CMUT cell by way of non-limiting example) as deployed on an imaging device such as a catheter 100 or an ultrasound probe (patch), said element comprising the acoustic window 220 according to an embodiment of the present invention. Such a CMUT cell 200 is typically fabricated on a substrate 201, such as a silicon wafer. An ultrasound transducer array of an ultrasound imaging system may comprise one or more CMUT cells 200. The CMUT cells 200 may be either individually activated or in combination with each other. The individual cells 200 can have round, rectangular, hexagon or other peripheral shapes.

Each CMUT cell 200 has at least a pair of electrodes 205 and 215 separated by a cavity 207. The cavity 207 is formed in between a membrane 211 that is suspended over a cell floor 203 formed by the top surface of the substrate 201. The membrane 211 may be made of one or more layers of electrically insulating materials, e.g. silicon oxide ($SiO_x$, x>1), silicon nitride, low-k dielectric materials and the like. The membrane 211 is flexible, i.e. is adapted to move or vibrate. The membrane 211 may be suspended over the cell floor 203 (i.e. the substrate 201) through a support structure 209, which may be made of the same material as the membrane 211, e.g. by depositing the membrane 211 over a sacrificial material defining the cavity 207 and subsequently removing the sacrificial material to form the cavity 207 surrounded by the membrane 211 including the support structure 209.

The electrodes 205, 215 may be made of any suitable electrically conductive material, such as a metal or metal alloy. The bottom electrodes 205 may be embedded in the floor 203 of the cell 200, while the top electrode 215 may be embedded in the membrane 211. The electrode 205 and 215 may be deposited on the cell floor 31 or the membrane 5 as additional layers. The bottom electrode 205 may be insulated on its cavity-facing surface with an additional layer (not pictured). This insulating layer may comprise either one of or a combination of an oxide-nitride-oxide (ONO) dielectric layer, silicon oxide layer, aluminum or hafnium oxide layers, for example. The insulating layer may be formed above the bottom electrode 205 and below the membrane electrode 215. An ONO-dielectric layer advantageously reduces charge accumulation on the electrodes which leads to device instability, drift and reduction in acoustic output pressure. The cavity 207 may be either air- or gas-filled, or wholly or partially evacuated. Two electrodes 205 and 215 separated by the cavity 207 represent a capacitance.

An application of electrical signal through a drive circuit 45 coupled to the electrodes 205 and 215 causes a mechanical movement/vibration of the membrane 211, which results in the change of the capacitance and can be manipulated by integrated circuitry an associated with the CMUT cell 200. An example embodiment of such integrated circuitry will be explained in more detail below. The drive circuit 45 may be implemented as an integrated part of the integrated circuitry. The drive circuit 45 usually comprises an A/C signal source and a D/C voltage source. In a transmit mode of the CMUT cell 200, the D/C voltage source may be used to bias the membrane 211 with the A/C signal source driving an oscillation of the biased membrane 211 to generate ultrasound signals, e.g. pulses, at the oscillation frequency, as is well-known per se. The A/C component is typically omitted in a receive mode of the CMUT cell 200, in which the oscillations of the membrane 211 are induced by echoes of previously emitted ultrasound signals, e.g. pulse echoes, by the CMUT cell 200. In an embodiment, the D/C voltage source may be adapted to bias the membrane 211 into a so-called collapse mode, in which a central portion of the membrane 211 is kept in contact with the cell floor 203 during the oscillations induced with the A/C signal originating from the A/C signal source. As is well-known per se, operation of a CMUT cell 200 in collapse mode may increase the acoustic pressure and the dynamic range of the CMUT cell 200.

According to an embodiment of the present invention, the transducer element, here a CMUT cell 200 by way of non-limiting example as previously explained as other types of transducer elements, e.g. PZT elements, may also be deployed, further comprises an acoustic window 220 preferably having a total thickness of less than 100 micron, more preferably less than 30 micron, in some embodiments, e.g. catheter applications. The acoustic window 220 comprises a first layer 221 contacting the ultrasound emitting surface of the ultrasound transducer element (e.g. the upper surface of the membrane 211 of a CMUT cell 200) and a second layer 223 on the first layer 221 such that the first layer 221 is sandwiched in between the ultrasound emitting surface and the second layer 223. The first layer 221 and the second layer 223 both may be formed from the same hydrocarbon elastomer or from different hydrocarbon elastomers preferably having closely matched acoustic properties, e.g. acoustic impedances. Hydrocarbon elastomers, and in particular polybutadiene, may have a density equal or below 0.95 g/cm$^3$ and may exhibit a low acoustic energy loss (attenuation) and a suitable acoustic impedance optimization. Acoustic impedance (Z) is defined as the product of acoustic propagation velocity (v) for acoustic energy (or wave) in a medium and density (ρ) of this medium:

$$Z=\rho*v.$$

Hydrocarbon elastomers may have an acoustic impedance value of above 1.4 MRayl, which is close to soft tissue's impedance of about 1.6 MRayl, such that acoustic losses through acoustic impedance mismatches can be reduced by the deployment of such hydrocarbon elastomers, e.g. polybutadiene. Such elastomers may exhibit an acoustic loss per millimeter for acoustic energy passing therethrough of less than 1.5 dB for a wide range of the acoustic wave frequencies applicable in medical ultrasound, such as in between 2 and 25 MHz, which are typical frequency domains of a wide variety of ultrasound transducer elements including CMUTs and PZTs. Furthermore, such elastomers have a relatively low density and in an uncured state have a hardness value below 50 Shore A, which softness combined with the aforementioned low acoustic wave attenuation characteristics of such elastomers may provide a beneficial effect on the improved acoustic coupling of the ultrasound transducer element (in particular a CMUT vibrating membrane) with the acoustic window layer.

However, the softness of such hydrocarbon elastomers is less suitable to provide the ultrasound transducer element with mechanical protection and may not provide the ultrasound transducer element with the desired moisture barrier properties. Moreover, many hydrocarbon elastomers, such as in particular polybutadiene, experience hardening over time through (photo-)oxidation causing cross-linking (vulcanization) of the elastomer material when exposed to UV light or oxygen for instance, causing a degradation of the acoustic properties of the hydrocarbon elastomer. At the same time, such vulcanization improves the mechanical robustness and moisture barrier properties of the hydrocarbon elastomer.

This insight has been utilized in embodiments of the present invention, in which the first layer 221 of a hydrocarbon elastomer, preferably in uncured form, in the acoustic window 220 further comprises an antioxidant to prevent vulcanization of the first layer 221 such that the first layer 221 retains its desired acoustic properties. In contrast, the second layer 223 of a further hydrocarbon elastomer in the acoustic window 220 is allowed to harden through vulcanization, for example by omitting the antioxidant from the second layer 223 or alternatively by including the antioxidant in the second layer 223 in such an amount (i.e. a small amount than in the first layer 221) such that vulcanization of the second layer 223 is not prevented, but instead the rate of vulcanization is controlled by the inclusion of the small amount of antioxidant in the second layer 223. The hydrocarbon elastomer and the further hydrocarbon elastomer preferably are the same hydrocarbon elastomer as this guarantees the desired acoustic impedance matching. A particularly suitable hydrocarbon elastomer is polybutadiene although hydrocarbon elastomers such as Butyl (isobutylene-isoprene copolymer), ethylene propylene, isoprene, e.g. synthetic cis-isoprene or natural isoprene, may be considered as alternatives to polybutadiene. The first layer 221 preferably has a Shore A hardness of less than 50 Shore A, preferably of less than 10 Shore A, when measured with a durometer in accordance with the ASTM D2240 standard. The second layer 223 preferably has a Shore A hardness in excess of 50 Shore A, preferably in excess of 60 Shore A, when measured with a durometer in accordance with the ASTM D2240 standard.

In an embodiment, the second layer 223 may be left to naturally vulcanize during use of the imaging device although in an alternative preferred embodiment, the hydrocarbon elastomer in the second layer 223 is actively vulcanized, e.g. using a suitable heat treatment, to obtain a cross-linked hydrocarbon elastomer second layer 223 having the desired mechanical and moisture barrier properties. Moreover, by using the same hydrocarbon elastomer, e.g. polybutadiene, for both layers 221 and 223, excellent adhesion between the layers 221 and 23 is achieved without the need for an adhesive, which would negatively affect acoustic properties of the acoustic window 220.

In an embodiment, the first layer 221 may have a thickness in a range of 5-10 micron (μm). Any suitable antioxidant may be included in the first layer 221. Such antioxidants for hydrocarbon elastomers are well-known per se. For example, a particularly suitable class of antioxidants is so-called phenolic stabilizers, which are primary antioxidants that act as hydrogen donors in the polymeric first layer 221. Such compounds react with peroxy radicals to form hydroperoxides and prevent the abstraction of hydrogen from the hydrocarbon elastomer backbone, thereby preventing cross-linking of the backbone with other backbones in the polymeric first layer 221. A non-limiting example of such a phenolic stabilizer is shown in Formula 1:

Formula 1

This antioxidant is marketed by the BASF Company under the trade name Irganox 1076. Without wishing to be bound by theory, it is believed that the hydrocarbon chain of such a phenolic stabilizer improves mixing of the antioxidant with a hydrocarbon backbone of an elastomer such as polybutadiene, whilst the sterically hindered phenol group forming a head of the antioxidant molecule acts as a hydrogen donor thereby buffering ambient oxygen. However, it is reiterated for the avoidance of doubt that embodiments of the present invention are not limited to a particular type of phenolic stabilizer or indeed a particular type of antioxidant; any suitable antioxidant may be used in the first layer 221 of the acoustic window 220. The antioxidant may be present in the first layer 221 in an amount of 0.05%-0.5% by weight based on the total weight of the first layer 221 in some embodiments.

Figure 3:
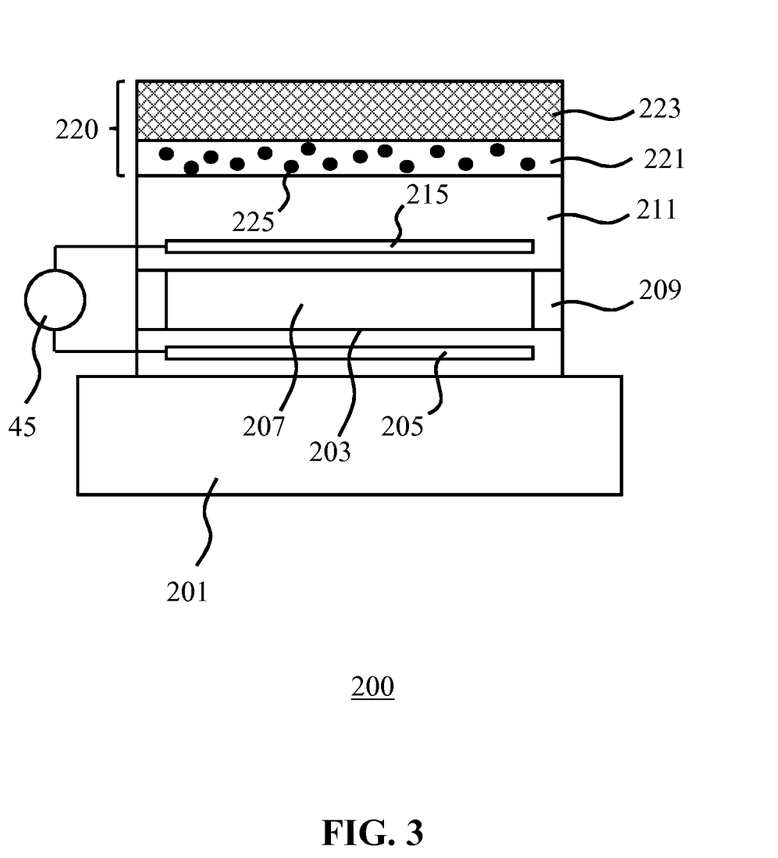
FIG. 3 schematically depicts an aspect of an imaging device according to another example embodiment.

Although hydrocarbon elastomers such as polybutadiene have a particularly suitable acoustic impedance for impedance matching a transducer element with body tissue, in particular soft tissue, as previously explained, it may be desirable to further reduce the acoustic impedance mismatch between the acoustic window 220 and in particular the first layer 221 of the acoustic window 220 and such body tissue. To this end, at least the first layer 221 of the acoustic window 220 may further include particles 225 as schematically depicted in FIG. 3. The particles 225 preferably are made of an electrically insulating material such as a ceramic material having a higher density than the hydrocarbon elastomer such as to increase the total density of the first layer 221. For example, ceramic particles such as metal oxide ($ZrO_2$, $Al_2O_3$, $TiO_2$, $Bi_2O_3$, $BaSO_4$, and so on) particles exhibit electrically insulating properties, which may be advantageous in providing additional electrical insulation to the transducer element electronics. It has been found that the inclusion (embedding) of such particles 225 in the first layer 221 causes minimal additional acoustic losses, in particular when the first particles 225 are included in the first layer 221 in an amount of 4-24% by weight based on the total weight of the first layer 221, preferably in an amount of 5-20% by weight based on the total weight of the first layer 221.

The particles 225 preferably have an average size lower than one tenth of the acoustic wavelength of the shortest wave within an operation bandwidth for the selected ultrasound application of the ultrasound transducer element(s) of the catheter 100. When the average size of the particles 225 becomes larger than the wavelength of the propagating ultrasound wave, this may cause additional scattering of the ultrasound wave in the acoustic window 220. For example, the particles may have an average size in between 10 nm and 10 micron, in particular in between 10-100 nm or in between 1-10 micron, depending on the operation bandwidth of the ultrasound transducer element(s) of the catheter 100.

As an example, Table 1 shows the measured changes in acoustic properties of an uncured polybutadiene layer with the introduction of zirconium dioxide ($ZrO_2$) insulating particles having in average diameter of about 2.5 micron and taking a fixed percentage of a total weight of the first layer 221.

TABLE 1

Changes in the density, acoustic wave velocity, acoustic impedance and attenuation (at frequency of 7 MHz) with an increasing percentage by weight of $ZrO_2$ particles based on the total weight of the polybutadiene layer.

| % $ZrO2$ | Density (g/cm$^3$) | Velocity (mm/microsec) | Impedance (MRayl) | Attenuation @7 MHz (dB/mm) |
|---|---|---|---|---|
| 0 | 0.906 | 1.570 | 1.423 | 0.55 |
| 4% | 0.937 | 1.553 | 1.455 | 0.75 |
| 8% | 0.972 | 1.532 | 1.489 | 0.87 |
| 16% | 1.0405 | 1.503 | 1.564 | 1.05 |
| 20% | 1.0855 | 1.469 | 1.5945 | 1.25 |

As can be seen from Table 1, the acoustic impedance of the layer can be tuned towards higher values, e.g. closer to the tissue's acoustic impedance by increasing the total density of the first layer 221 by addition of the particles 225 (here $ZrO_2$ particles) to the layer 221, whilst the attenuation of the layer 221 still remains below 1.5 dB/mm, even for the layers comprising 20% by weight of the insulating particles 225 ($ZrO_2$). When the first layer 221 of the acoustic window 220 comprising the antioxidant and the hydrocarbon elastomer with embedded insulating particles 225 has a density equal or above 0.94 g/cm$^3$ and an acoustic impedance equal or above 1.5 MRayl, a direct acoustical coupling of the acoustic window 220 to the ultrasound emitting surface of the ultrasound transducer element, e.g. a membrane 211 of the CMUT cell 200 is provided, thereby obviating the need for an additional coupling medium between the acoustic window 220 and the ultrasound transducer element(s). Moreover, an acoustic impedance equal or above 1.5 MRayl closely matches the acoustic impedance of ultrasonicated body tissue as previously explained.

At this point it is noted that although the acoustic window 220 may be deployed on any type of ultrasound transducer element as previously explained, the use of a soft first layer 221 in such an acoustic window 220 is especially advantageous for CMUT cells 220, in particular CMUT cells 200 operated in the so-called collapse mode. This is because the relatively light molecular weight of the monomers of the hydrocarbon elastomers, combined with these elastomers' relatively low hardness of preferably below 50 ShoreA may provide an improved acoustic contact between the acoustic window 220 and the membrane 211 adapted to vibrate.

Figure 4:
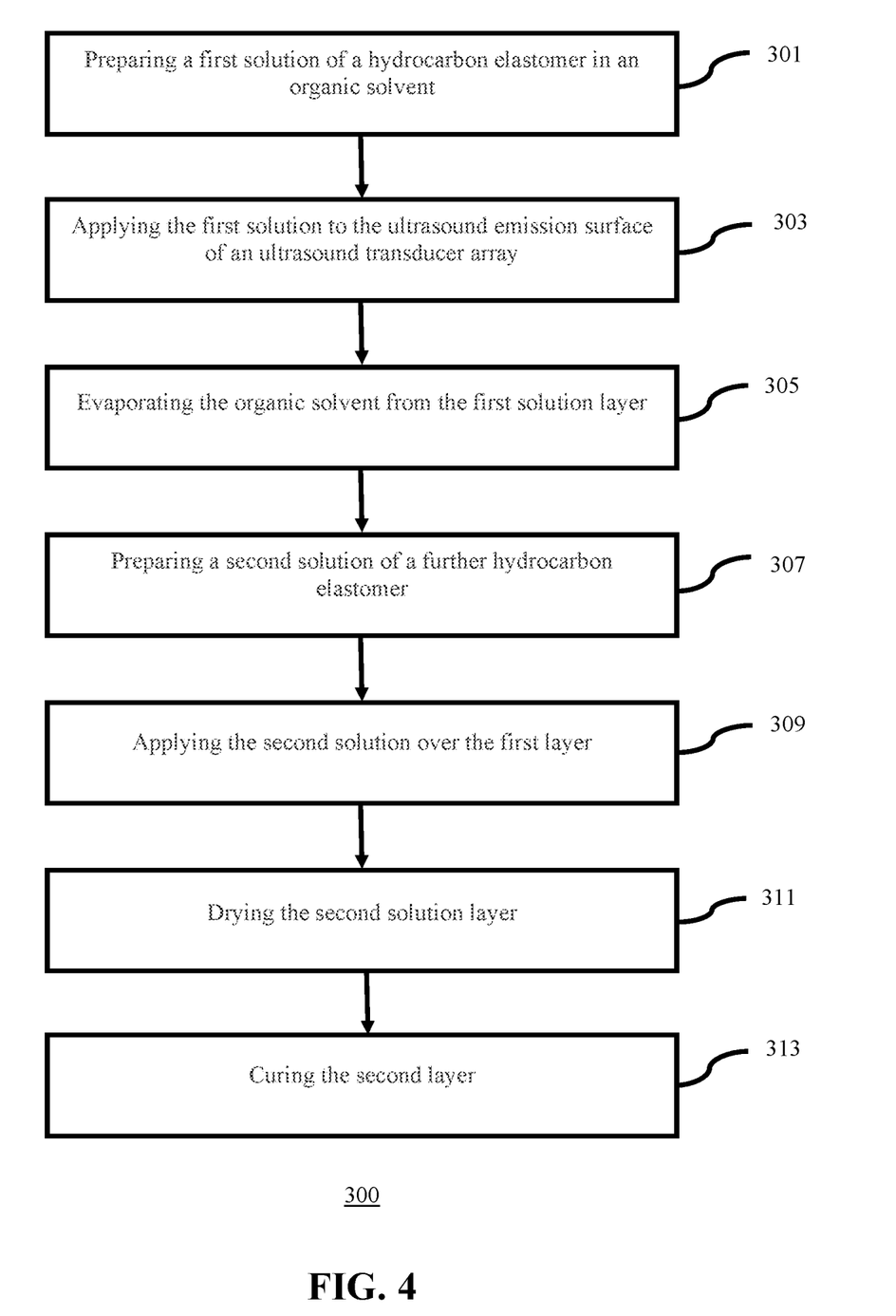
FIG. 4 is a flowchart of a method for forming an acoustic window or the ultrasound transducer array of such an imaging device.

FIG. 4 is a flow chart of a method 300 to form an acoustic window 220 on one or more ultrasound transducer elements such as one or more CMUT cells 200. The method 300 starts in 301 with the preparation of a first solution of the hydrocarbon elastomer, preferably polybutadiene, in an organic solvent such as an alkane solvent, e.g. pentane, hexane, cyclohexane, heptane, octane, and so on. Heptane is particularly mentioned. The solution may be prepared by dissolving a granulate of pre-polymerized polybutadiene (CB728 T from Lanxess) in the organic solvent. An antioxidant, e.g. a sterically hindered phenolic stabilizer such as Irganox 1076 is added, and optionally insulating particles 225 may be added to the solution to increase the acoustic impedance of the first layer 221 to be formed from this solution as previously explained. The polymeric material acts as a dispersion agent for the particles 225, such that a liquid mixture of the polymeric material and the insulating particles 225 in the organic solvent is provided. The filler particles 225 in the liquid mixture may increase the hardness of the first layer 221 of the acoustic window 220. To counteract this, additional dispersion agents such as fatty acids (a carboxylic acid with an aliphatic chain, which is either saturated or unsaturated) may be added to the liquid mixture, which fatty acids may assist in keeping the average hardness of the first layer 221 at a relatively constant value. The unsaturated chains of fatty acid like oleic acid, linoleic acid and linolenic acid (one, two and respectively three double carbon bonds) can polymerize and bond to the polybutadiene chains. This provides a good dispersion/distribution of particles 225 in the liquid mixture.

Next, the first solution is applied in 303 to the ultrasound emission surface of an ultrasound transducer array 101 comprising one or more ultrasound transducer elements, e.g. by dip coating the ultrasound emission surface with the first solution or by dispensing the first solution on the ultrasound emission surface using well-known dispensing techniques. The thickness of the first solution layer on the ultrasound emission surface may be controlled in case of the dip coating technique by the contact time between the first solution and the ultrasound emission surface.

Next, in 305, the organic solvent is evaporated from the first solution layer on the ultrasound emission surface during a drying step to form the first layer 221 of the acoustic window 220. This for example may be achieved by a drying process at an elevated temperature, e.g. about 70° C. This drying step may be terminated once the first layer 221 becomes tacky, to promote adhesion of the second layer 223 to the first layer 221 without requiring separate adhesives.

A second solution of a further hydrocarbon elastomer, which may be the same hydrocarbon elastomer as used in the first solution, e.g. polybutadiene, is prepared in 307, which second solution may be prepared in the same manner as the first solution using the same constituents apart from the reduction or omission of the antioxidant from the second solution in order to prepare a second layer 223 that can be vulcanized (cross-linked) in order to increase the Shore A hardness of the second layer 223 compared to the first layer 221. Preferably, the second solution does not contain any antioxidant. In 309, a layer of the second solution is applied over the partially developed first layer 221, e.g. through dip coating, dispensing or the like, after which the second solution layer is dried in 311 at a temperature, e.g. 100° C., sufficient to remove the remaining solvent from the partially developed first layer 221 and the second solution layer to form the second layer 223 over the first layer 221, which second layer 223 may be cured, e.g. cross-linked in 313 (or alternatively during the development step in 311) to form the acoustic window 220 over the ultrasound transducer array 101. The ultrasound transducer array 101 may be in situ on the imaging device such as the catheter 100 or may be mounted on this imaging device (catheter 100) after deposition of the acoustic window 220 on the ultrasound emission surface(s) of the ultrasound transducer array 101.

It is noted for the avoidance of doubt that the acoustic window forming method 300 as depicted by the flowchart of FIG. 4 is a non-limiting example embodiment of such a method; many variations to this method will be immediately apparent to the skilled person. For instance, the skilled person will immediately realize that the order of the steps depicted in the flowchart of FIG. 4 may be altered without departing from the present invention; for example, the second solution may be prepared prior to or simultaneously with the first solution. Also, although the first layer 221 and the second layer 223 are preferably formed on the ultrasound emission surface(s) and the first layer 221 respectively without the use of an adhesive such as glue, it should be understood that in alternative embodiments such adhesives may be applied to increase the adhesive strength between the various layers and surfaces.

Figure 5:
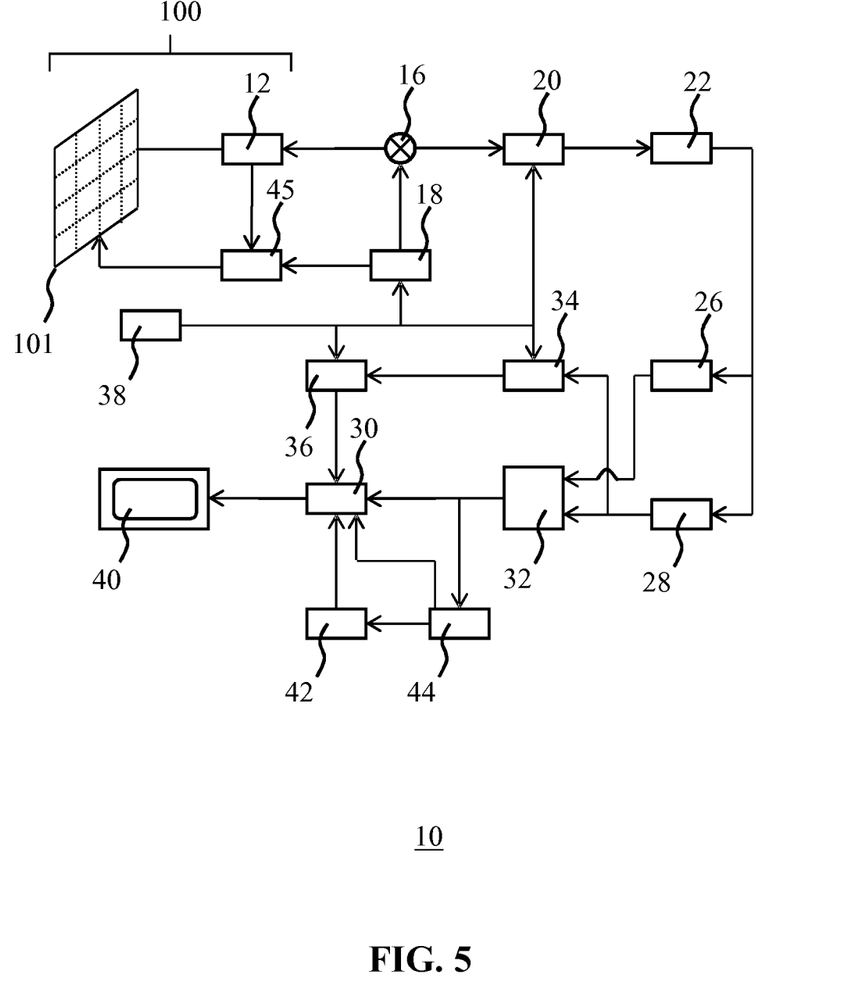
FIG. 5 schematically depicts a circuit diagram of an ultrasound imaging system according to an example embodiment.

FIG. 5 schematically depicts a block diagram of the electronics, i.e. control circuitry, of an ultrasound imaging system 10 according to an example embodiment that may be deployed to interface with an imaging device by controlling the ultrasound transducer array 101 including the acoustic window 220 (for example disposed on a catheter 100) for the generation of ultrasound waves, e.g. ultrasound pulses, and reception of ultrasound echoes, e.g. pulse echoes, e.g. for diagnostic imaging purposes. The ultrasound transducer array(s) 101 of the imaging device may be coupled to a microbeam former 12, which may be located within said imaging device, e.g. in the ultrasound transducer array 101 or on an interface, e.g. a PCB between the ultrasound transducer array 101 and a coaxial wire connecting the ultrasound transducer array 101 to thee electronics, in some embodiments. The microbeam former 12 controls transmission and reception of signals by the one or more ultrasound transducer cells of the ultrasound transducer array 101. Microbeam formers are capable of at least partial beam forming of the signals received by groups or "patches" of transducer element tiles for instance as described in U.S. Pat. No. 5,997,479 (Savord et al.), U.S. Pat. No. 6,013,032 (Savord), and U.S. Pat. No. 6,623,432 (Powers et al.)

The microbeam former 12 may be coupled by a probe cable, e.g. coaxial wire, to a terminal, e.g. a user console device or the like, comprising a transmit/receive (T/R) switch 16 which switches between transmission and reception modes and protects the main beam former 20 from high energy transmit signals when a microbeam former is not present or used and the ultrasound transducer array 101 is operated directly by the main system beam former 20. The transmission of ultrasonic beams from the ultrasound transducer array 101 under control of the microbeam former 12 may be directed by a transducer controller 18 coupled to the microbeam former by the T/R switch 16 and the main system beam former 20, which receives input from the user's operation of the user interface 10 through control panel 38. One of the functions controlled by the transducer controller 18 is the direction in which beams are steered and focused. Beams may be steered straight ahead from (orthogonal to) the ultrasound transducer array 101, or at different angles for a wider field of view. The transducer controller 18 may be coupled to control the aforementioned drive circuit 45 for the ultrasound transducer array 101. For instance, the drive circuit 45 may set the DC and AC bias voltage(s) that are applied to CMUT elements of a CMUT array, e.g. to operate the CMUT elements in collapse mode, as is well-known per se, in case of a CMUT-based ultrasound transducer array 101. The transducer controller 18 may be further adapted to control the drive circuit 45 such as to switch the ultrasound transducer elements to a low-power mode, e.g. in response to a temperature sensor signal indicative of the ultrasound transducer elements reaching a critical temperature.

The partially beam-formed signals produced by the microbeam former 12 may be forwarded to the main beam former 20 where partially beam-formed signals from individual patches of ultrasound transducer elements are combined into a fully beam-formed signal. For example, the main beam former 20 may have 128 channels, each of which receives a partially beam-formed signal from a patch of dozens or hundreds of ultrasound transducer elements and/or from clusters of such ultrasound transducer elements, e.g. from ultrasound transducer tiles carrying a plurality of such ultrasound transducer elements. In this way the signals received by thousands of transducer elements of an ultrasound transducer array 101 can contribute efficiently to a single beam-formed signal.

The beam-formed signals are coupled to a signal processor 22. The signal processor 22 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles.

The signal processor 22 optionally may perform additional signal enhancement such as speckle reduction, signal compounding, and noise elimination. The bandpass filter in the signal processor 22 may be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals may be forwarded to a B-mode processor 26 and optionally to a Doppler processor 28. The B-mode processor 26 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 28, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor may receive and process a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B-mode (and Doppler) processor(s) are coupled to a scan converter 32 and a multiplanar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image.

The scan converter can overlay a B-mode structural image with colors corresponding to motion at points in the image field with their Doppler-estimated velocities to produce a color Doppler image which depicts the motion of tissue and blood flow in the image field. The multiplanar reformatter 44 will convert echoes which are received from points in a common plane in a volumetric region of the body into an ultrasonic image of that plane, for instance as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.)

The 2D or 3D images are coupled from the scan converter 32, multiplanar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B-mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the control panel 38, such as patient name.

The user interface is also coupled to the transmit controller 18 to control the generation of ultrasound signals from the ultrasound transducer array 101 and hence the images produced by the transducer array and the ultrasound system. The user interface is also coupled to the multiplanar reformatter 44 for selection and control of the planes of multiple multiplanar reformatted (MPR) images which may be used to perform quantified measures in the image field of the MPR images.

As will be understood by the skilled person, the above embodiment of an ultrasonic (diagnostic) imaging system 10 is intended to give a non-limiting example of such an ultrasonic (diagnostic) imaging system. The skilled person will immediately realize that several variations in the architecture of the ultrasonic imaging system 10 are feasible without departing from the teachings of the present invention. For instance, as also indicated in the above embodiment, the microbeam former 12 and/or the Doppler processor 28 may be omitted, the ultrasound probe 100 may not have 3D imaging capabilities and so on. Other variations will be apparent to the skilled person.

At this point, it is noted that although the acoustic window 220 according to embodiments of the present invention has particular benefits when applied to an ultrasound transducer array of a catheter 100, such an acoustic window 220 may be equally applied to ultrasound transducer arrays in other applications, e.g. stand-alone ultrasound transducer arrays such as ultrasound probes to be applied to the skin of a patient. It will be readily understood that in such embodiments, certain embodiments preferred in the context of catheters, such as the overall thickness of the acoustic window 220, may not necessarily be preferred in such other application domains. Specifically, for a stand-alone ultrasound transducer array (forming a part of the imaging device configured for external use, for example), the acoustic window 220 may have a thickness in excess of 100 micron as in such application domains the thickness is not particularly limited by the application domain (contrary to catheter applications, in which the thickness limitations typically are applicable to limit the overall dimensions of the catheter as previously explained).

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:
1. An ultrasound probe or cathether comprising:
an ultrasound transducer array comprising a plurality of ultrasound transducer elements defining an ultrasound emitting surface of the ultrasound transducer array; and an acoustic window coupled to the ultrasound transducer array, said acoustic window comprising:
  a first layer contacting the ultrasound emitting surface, said first layer comprising a hydrocarbon elastomer and an antioxidant such that the hydrocarbon elastomer in the first layer is prevented from cross-linking, thereby providing the first layer with a first Shore A hardness; and
  a second layer contacting the first layer and comprising the same hydrocarbon elastomer, wherein the second layer is an outer layer of the acoustic window, wherein the second layer does not include the antioxidant or the second layer includes a smaller amount of the antioxidant than in the first layer such that the hydrocarbon elastomer in the second layer is at least partially cross-linked, thereby providing the second layer with a second Shore A hardness greater than the first Shore A hardness, and
  wherein the same hydrocarbon elastomer is adapted to provide:
    acoustic coupling with the ultrasound emitting surface based on the first Shore A hardness of the first layer; and
    at least one of mechanical protection or a moisture barrier for the ultrasound transducer array based on the second Shore A hardness of the second layer.

2. The ultrasound probe or catheter of claim 1, wherein the first layer has a thickness in a range of 5-10 microns and/or the acoustic window has a thickness of less than 100 microns.

3. The ultrasound probe or catheter of claim 1, wherein the same hydrocarbon elastomer is polybutadiene.

4. The ultrasound probe or catheter of claim 1, wherein the first layer has a Shore A hardness of less than 50 Shore when measured with a durometer in accordance with the ASTM D2240 standard.

5. The ultrasound probe or catheter of claim 1, wherein the antioxidant is a phenolic stabilizer.

6. The ultrasound probe or catheter of claim 1, wherein the first layer contains the antioxidant in an amount of 0.05%-0.5% by weight based on the total weight of the first layer.

7. The ultrasound probe or catheter of claim 1, wherein at least the first layer of the acoustic window further comprises particles embedded in the hydrocarbon elastomer.

8. The ultrasound probe or catheter of claim 7, wherein the first layer comprises the particles in an amount of 4-24% by weight based on the total weight of the first layer.

9. An ultrasound imaging system comprising the ultrasound probe or catheter of claim 1 and control circuitry for controlling the ultrasound transducer array of the ultrasound probe or catheter.

10. A method of forming an acoustic window on an ultrasound transducer array for an ultrasound probe or catheter, the ultrasound transducer array comprising a plurality of ultrasound transducer elements that define an ultrasound emitting surface of the ultrasound transducer array, the method comprising:
  depositing a first solution that comprises a hydrocarbon elastomer and an antioxidant in an organic solvent on the ultrasound emitting surface;
  removing the organic solvent to form a first layer of the acoustic window contacting the ultrasound emitting surface, said first layer comprising the hydrocarbon elastomer and the antioxidant such that the hydrocarbon elastomer in the first layer is prevented from cross-linking, thereby providing the first layer with a first Shore A hardness;
  depositing a second solution comprising the same hydrocarbon elastomer in a further organic solvent on the first layer;
  removing the further organic solvent to form a second layer of the acoustic window contacting the first layer, wherein the second layer is an outer layer of the acoustic window, wherein the second layer does not include the antioxidant or the second layer includes a smaller amount of the antioxidant than in the first layer; and
  at least partially cross-linking the hydrocarbon elastomer in the second layer because the second layer does not include the antioxidant or the second layer includes a smaller amount of the antioxidant than in the first layer such that the second layer comprises a greater second Shore A hardness greater than the first layer the first Short A hardness,
  wherein the same hydrocarbon elastomer is adapted to provide:
    acoustic coupling with the ultrasound emitting surface based on the first Shore A hardness of the first layer; and
    at least one of mechanical protection or a moisture barrier for the ultrasound transducer array based on the second Shore A hardness of the second layer.

11. The method of claim 10, wherein the same hydrocarbon elastomer is polybutadiene.

* * * * *